United States Patent [19]

Schermanz et al.

[11] Patent Number: 4,965,277
[45] Date of Patent: Oct. 23, 1990

[54] ALLYLAMINOETHYLAZOLES

[75] Inventors: Karl Schermanz, Graz; Gerald Saischek, Lannach; Dietmar Kores, Leonding; Josef Graf, Kleinraming; Gerhard Haas, Niederthalheim; Kurt Martetschläger, Linz, all of Austria

[73] Assignee: CL Pharma Aktiengesellschaft, Linz, Austria

[21] Appl. No.: 378,898

[22] Filed: Jul. 12, 1989

[30] Foreign Application Priority Data

Jul. 22, 1988 [AT] Austria .................................. 1875/88

[51] Int. Cl.$^5$ .................. A01N 43/50; C07D 233/00; C07D 403/00; C07D 233/54
[52] U.S. Cl. ..................................... 514/385; 548/300; 548/336; 548/341; 514/397; 514/399
[58] Field of Search ....................... 548/300, 336, 341; 514/385, 397, 399

[56] References Cited

FOREIGN PATENT DOCUMENTS

| | | | |
|---|---|---|---|
| 0020859 | 7/1981 | European Pat. Off. | 548/300 |
| 0061798 | 6/1982 | European Pat. Off. | 548/300 |
| 0084236 | 7/1983 | European Pat. Off. | 548/300 |
| 81-152446 | 11/1981 | Japan | 548/300 |

Primary Examiner—Mary C. Lee
Assistant Examiner—Robert C. Whittenbaugh
Attorney, Agent, or Firm—Mark Dryer

[57] ABSTRACT

New allylaminoethylimidazoles of the formula:

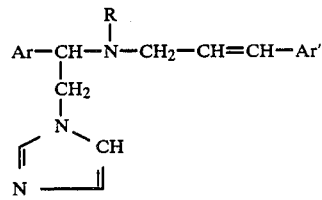

in which R is a hydrogen atom or an alkyl group containing 1 to 5 carbon atoms; each of Ar and Ar' is an unsubstituted phenyl group, a phenyl group substituted by one or more substituents selected from $C_1$–$C_3$ alkyl, $C_1$–$C_3$ alkoxy, nitro and halogen, an unsubstituted thienyl group, or a thienyl group substituted by halogen or naphthyl; phytophysiologically or pharmacologically tolerated acid addition thereof; and fungicidal and antimycotic agents containing such compounds.

8 Claims, No Drawings

ALLYLAMINOETHYLAZOLES

The invention relates to new allylaminoethylimidazoles and fungicidal and antimycotic agents containing these compounds.

Substituted 2-phenyl-ethyl-amino-1,2,4-triazoles which have fungicidal properties are known from EP-A 1,798. The construction principle of the allylaminoethylazoles have not been mentioned. Unexpectedly, new allylaminoethylazoles which are distinguished by a potent fungicidal and antimycotic action have now been found.

The present invention provides an allylaminoethylimidazole of the formula:

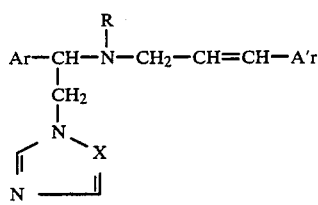

in which X is a CH group, R is a hydrogen atom or an alkyl group (1 to 5 C atoms), each of Ar and Ar' is an unsubstituted phenyl group, a phenyl group substituted by one or more substituents selected from $C_1$–$C_3$ alkyl $C_1$–$C_3$ alkoxy, nitro and halogen, an unsubstituted thienyl group, or a thienyl group substituted by halogen or naphthyl; or a phytophysiologically or pharmacologically tolerated acid addition salt thereof.

Also disclosed herein are compounds of formula I wherein X is a nitrogen atom, but these compounds do to form part of the present invention.

In formula I, X is a CH group, R is a hydrogen atom or an alkyl group having 1 to 5 C atoms, preferably a hydrogen atom, and each of Ar and Ar' is a phenyl radical which is unsubstituted or substituted by one or more substituents from the group comprising alkyl (1 to 3 C atoms), alkoxy (1 to 3 C atoms) nitro groups and halogen, a thienyl radical which is unsubstituted or substituted by halogen or a naphthyl radical, preferably a phenyl radical which is unsubstituted or substituted by one or more halogen atoms.

Preferably Ar is a phenyl radical which is substituted by halogen, and Ar' is a phenyl radical, which can optionally be substituted by alkyl (1 to 3 C atoms), alkoxy (1 to 3 C atoms) or also by halogen. Preferred alkyl groups containing 1 to 5 carbon atoms are methyl, ethyl, propyl, butyl, pentyl and the like and their isomers, such as, for example, isopropyl, isobutyl, tert.-butyl, sec.-butyl, isopentyl. Alkoxy group containing one to three carbon atoms are methoxy, ethoxy, propoxy and isopropoxy.

Halogen atoms are fluorine, chlorine, bromine and iodine, in particular chlorine.

The compounds 1-(2-(2,4-dichlorophenyl)-2-(3-phenylallylamino))ethyl-1H-imidazole, 1-(2-(2,4-dichlorophenyl)-2-(3-(4-methoxyphenyl)allylamino)-)ethyl-1-imidazole, 1-(2-(2,4-dichlorophenyl)-2-(3-(4-methylphenyl)allylamino))ethyl-1H-imidazole, 1-(2-(2,4-dichlorophenyl)-2-(3-(2-chlorophenyl)allylamino)-)ethyl-1H-imidazole and 1-(2-(2,4-dichlorophenyl)-2-(3-(4-chlorophenyl)allylamino))ethyl-1H-triazole are especially preferred.

The new compounds can also be in the form of their acid addition salts or metal complexes.

Examples of possible acid addition salts are salts of inorganic or organic acids, for example hydrochlorides, -bromides and -iodides, nitrates, hydrogen sulphates, methosulphates, trifluoromethylsulphonates, tosylates, acetates, trifluoroacetates, lactates, malates and benzoates.

The compounds of formula I herein may be prepared by a process wherein (a) a compound of the formula II

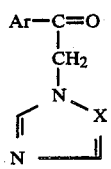

in which X and Ar have the abovementioned meaning, is reacted with a compound of the formula III

$$NH_2—CH_2—CH=CH—Ar'$$  III in which Ar' has the abovementioned meaning, if appropriate in an inert diluent, to give a compound of the formula IV

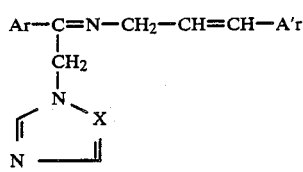

or (b) a compound of the formula V

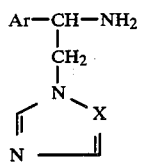

in which X and Ar have the abovementioned meaning, is reacted with a compound of the formula VI

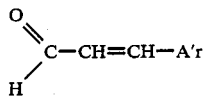

in which Ar' has the abovementioned meaning, if appropriate in an inert diluent, to give a compound of the formula VII

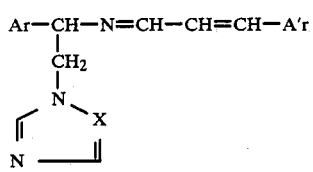

and the compound of the formula IV formed or the compound of the formula VII formed, is reduced in the presence of an inert diluent by addition of a reducing agent to give a compound of the formula I, in which R denotes a hydrogen atom, and, if desired, the product is alkylated to give a compound of the general formula I in which R denotes an alkyl radical (1 to 5 C atoms).

The reaction of the compound of the formula II with the compounds of the formula III and the reaction of the compounds of the formula V with the compounds of the formula VI are advantageously carried out in an organic diluent.

Diluents which are used are aliphatic or aromatic hydrocarbons, which may be chlorinated, such as benzine fractions, perchloroethylene, benzene, toluene, chlorobenzene and xylene, ethers, such as dibutyl ether and dioxane, alcohols, such as butanol, pentanol and ethylene glycol, and acid amides, such as dimethylformamide and mixtures thereof with the abovementioned diluents. Toluene is preferably used.

The reaction is carried out at temperatures of about 0 to 180° C., preferably at the boiling point of the particular diluent. The water of reaction formed is advantageously removed by azeotropic distillation. The starting compounds are in general employed in a stoichiometric ratio. However, an excess of one or other of the starting compounds may be advantageous in some cases. In a preferred embodiment, the starting compounds are dissolved or suspended in toluene in a stoichiometric ratio. The solution or suspension is then heated under reflux, using a water separator, until no further water of reaction separates out.

After removal of the diluent, the imino compounds formed, of the formula IV or VII, are reduced without further purification to give the compounds of the formula I in which R is a hydrogen atom. For this, the imino compounds are dissolved or suspended in an organic diluent and a reducing agent is added. Diluents which can be used are alcohols, such as methanol, ethanol and the like, or ethers, such as diethyl ether, diisopropyl ether or tetrahydrofuran, depending on the nature of the reducing agent used.

Examples of possible reducing agents are complex metal hydrides, such as sodium borohydride, lithium borohydride or aluminium borohydride, sodium cyanoborohydride or lithium cyanoborohydride, lithium aluminium hydride and the like, but it is also possible for the hydrogenation to be carried out with hydrogen in the presence of suitable catalysts. The reduction is preferably carried out with sodium borohydride in methanol, the metal hydride usually being employed in an excess of 1.1-to 20-fold. The reaction can be carried out at temperatures between about −20° C. and the boiling point of the solvent used, and is preferably carried out between −5° C. and 65° C.

When the reaction has ended, the excess metal hydride is destroyed by addition of an acid, preferably hydrochloric acid, the solvent being removed before or after the addition of the acid, if appropriate. For further working up, the base of the compound IV or VII is liberated by addition of alkali, preferably aqueous sodium hydroxide solution, and is extracted with the aid of an organic water-immiscible solvent, such as ethyl acetate or methylene chloride. After drying and removal of the organic solvent, the compound of the formula I in which R is a hydrogen atom can be converted into a compound of the formula I in which R is an alkyl radical (1 to 5 C atoms) utilizing customary alkylation methods.

For this, for example, alkylating reagents of the general formula RY in which R is an alkyl radical and Y is a leaving group, such as, for example, chloride, bromide, iodide or a benzylsulphonyl, toluenesulphonyl or methanesulphonyl group and the like, can be used. To introduce a methyl radical, the compound of the formula I in which R is a hydrogen atom can also be reacted in an aqueous formaldehyde solution in the presence of a reducing agent, such as, for example, formic acid.

The compounds of the formula I can be purified by recrystallization, column chromatography or formation and precipitation of the acid addition salts. To form the acid addition salts, the compounds of the formula I are dissolved in an organic solvent, such as, for example, diethyl ether, ethyl acetate, acetone or iso-propyl alcohol, and the corresponding acid addition salt is precipitated by addition of inorganic or organic acid and is isolated and if appropriate recrystallized from an organic solvent, such as ethyl acetate, iso-propanol, ethanol and the like.

The starting compound of the formula II are known and can be prepared, for example, in accordance with Drug Research 29 (II), No. 10, 1511 (1979) or J. Med. Chem., Vol. 24, 67 (1981). The ketones of the formula II are converted into the amines of the formula V, for example, in accordance with J. Med. Chem. 12, 790 (1969) and J. Med. Chem. 18, 531 (1975).

The starting compounds of the formula III can be prepared, for example, from the corresponding cinnamaldehydes in accordance with Robert Walter jun., J. Am. Chem. Soc. 74, 5185 (1952). Substituted cinnamaldehydes, compounds of the formula VI, can be prepared in accordance with, for example, Straus, Liebig's Annalen d. Chemie, 393, 311, 1858.

The allylaminoethylazoles according to the invention and their salts exhibit an excellent fungicidal action and thus represent an enrichment of the art. They are effective against a broad spectrum of phytopathogenic fungi, for example against Oomycetes, Ascomycetes, Basidiomycetes and Deuteromycetes.

The good tolerance by plants and the systemic mode of action in the concentrated needed for treatment of plant diseases allows treatment of above-ground parts of plants and of planting material and seed.

Plants which may be mentioned are, for example, cereal species, such as wheat, barley, rye or oats, and furthermore maize, strawberries, ornamental plants, potatoes as well as species of vegetables, such as cucumbers, beans or tomatoes.

The agents according to the invention can be used with particularly good success, for example, for combating the following plant diseases: *Botryotinia fuckeliana* (grey mould) on strawberries, *Cercospora beticola* (beet leaf spot disease) on beet, *Pseudocercosporella herpotrichoides* (stem break) on cereals, *Cochliobolus sativus* (helminthosporiosis) on cereals, *Pyrenophora teres* (net spot disease) on barley, *Phaeosphaeria nodorum* (brown glume, leaf drought) on cereals, *Septoria apiicola* (celery leaf spot disease) on celery, *Venturia inaequalis* (scab disease) on apples, *Fusarium culmorum* (stem base disease) on cereals, *Alternaria alternata* (black fungus) on cereals, *Aspergillus niger* (black watering can mould) and *Monographella nivalis* (snow mould) on cereals.

Depending on their field of use, the new active compounds can be converted into the customary formulations, such as solutions, wettable powders, emulsion concentrates, emulsions, suspensions, powders, foams, pastes, granules, aerosols, natural and synthetic substances impregnated with active compound, very fine capsules in polymeric substances and in coating compositions for seed, and furthermore in formulations for use with burning equipment, such as fumigating cartridges, cans, coils and the like, as well as ULV cold mist and warm mist formulations.

These formulations are produced in a known manner, for example by mixing the active compounds with extenders, that is to say liquid solvents, liquefied gases under pressure and/or solid carriers, if appropriate using surfactants, that is to say emulsifiers and/or dispersing agents and/or wetting agents and/or foam-forming agents. In the case of the use of water as an extender, organic solvents can, for example, also be used as auxiliary solvents. Possible liquid solvents are essentially: aromatics, such as xylene, toluene or alkyl-naphthalenes, chlorinated aromatics or chlorinated aliphatic hydrocarbons, such as chlorobenzenes, chloro-ethylenes or methylene chloride, aliphatic hydrocarbons, such as cyclohexane or paraffins, for example petroleum fractions, alcohols, such as butanol or glycol, and ethers and esters thereof, ketones, such as acetone, methylethyl ketone, methylisobutyl ketone or cyclohexanone, strongly polar solvents, such as dimethylformamide and dimethyl sulphoxide, and water. By liquefied gaseous extenders or carriers are meant those liquids which are gaseous at normal temperature and under normal pressure, for example aerosol propellants, such as halogenohydrocarbons, and butane, propane, nitrogen and carbon dioxide; possible solid carriers are: for example ground natural minerals, such as kaolins, clays, talc, chalk, quartz, attapulgite, montmorillonite or diatomaceous earth, and synthetic products, such as highly disperse silicic acid, aluminium oxide and silicates; possible solid carriers for granules are: for example crushed and fractionated natural rocks, such as calcite, marble, pumice, sepiolite and dolomite, and synthetic granules of inorganic and organic meals, as well as granules of organic material, such as sawdust, coconut shells, maize cobs and tobacco stalks; possible emulsifying agents and/or foam-forming agents are: for example nonionic and ionic surfactants, such as polyoxyethylenesorbitan tallow oil esters, Na-oleylmethyltauride, polyoxyethylene fatty acid esters, polyoxyethylene fatty alcohol ethers, for example alkylaryl polyglycol ethers, alkylsulphonates, alkylsulphates, arylsulphates and arylalkylsulphonates, and protein hydrolysis products; possible dispersing agents are: for example ligninsulphonates or condensation products of arylsulphonates and formaldehyde.

Adhesives and thickeners, such as carboxymethylcellulose, methylcellulose and natural and synthetic polymers in the form of powders, granules and lattices, such as gum arabic, polyvinyl alcohol and polyvinylacetate, can be used in the formulations.

It is possible to use dyestuffs, such as inorganic pigments, for example iron oxide, titanium oxide and Prussian blue, and organic dyestuffs, such as alizarin, azo and metal phthalocyanine dyestuffs, and trace nutrients, such as salts of iron, manganese, boron, copper, cobalt, molybdenum and zinc.

The formulations in general contain between 0.1 and 95% by weight of active compound, preferably between 0.5 and 50%.

The active compounds can be used as such, in the form of their formulations or in the use forms prepared therefrom by further dilution, such as ready-to-use solutions, emulsions, suspensions, powders, pastes and granules. They are used in the customary manner, for example by watering, immersing, spraying, atomizing, misting, vaporizing, injecting, forming a slurry, dusting, scattering, dry dressing, moist dressing, wet dressing, slurry dressing or encrusting.

In the treatment of parts of plants, the active compound concentrations in the use forms can be varied within a relatively wide range. They are in general between 1 and 0.0001% by weight, preferably between 0.5 and 0.001%.

When the active compounds are used for the treatment of fungal infections, the amounts applied are between 0.015 and 4 kg of active compound/ha of area.

For surface protection of trees and fruit, the active compounds can also be used in combination with plastics dispersions in a concentration of 0.25% to 5%, based on the weight of the dispersion.

In the treatment of seed, in general amounts of active compound of 0.001 to 50 g per kilogram of seed, preferably 0.01 to 10 g, are required.

In the treatment of soil, active compound concentrations of 0.00001 to 0.1% by weight, preferably 0.0001 to 0.02%, are required at the site of action.

It has furthermore been found, unexpectedly, that the new compounds of the general formula I, in particular the compounds in which X denotes a CH group, and their acid addition salts also have outstanding antimycotic properties. They have an excellent activity against pathogens which can trigger off mycoses in animals and humans, such as, for example, against yeasts, moulds and dermatophytes, and can thus be used as medicines, for example in the form of pharmaceutical preparations which contain the compounds according to the invention mixed with a pharmaceutical, organic or inorganic excipient material which is suitable for topical, enteral or parenteral administration.

Pharmaceutically tolerated non-toxic carriers or excipients which are usually employed for solid formulations are tricalcium phosphate, calcium carbonate, kaolin, bentonite, talc, gelatin, lactose, starch and the like; for semi-solid formulations there may be mentioned, for example, polyalkylene glycols, petroleum jelly, petrolatum and other ointment bases; and substances which can be used for liquid formulations are, for example, water, vegetable oils and low-boiling solvents, such as isopropanol, hydrogenated naphthalenes and the like.

The pharmaceutical preparations can be in a solid form, for example as tablets, coated tablets, suppositories or capsules, in a liquid form, for example as solutions, suspensions or emulsions, or in a semi-liquid form, for example as creams, lotions, gels or ointments. If appropriate, they are sterilized and/or contain auxiliaries, such as preservatives, stabilizers or emulsifying agents, salts for modifying the osmotic pressure or buffers. They can also be administered in combination with other therapeutically useful substances.

The formulations in general contain between 0.1 and 99.9% by weight of active compound.

In topical formulations, the amount can be, for example, about 0.1 to 10% of the total pharmaceutical formulation, whereas in other formulations the amount can make up about 5 to about 95% or more.

Topical application is preferred for use in pharmacy. For this, an area which is affected by fungi or bacteria or which is to be protected from fungal or bacterial attack can be treated with the compounds according to the invention or agents containing these, for example by powdering, dripping, spraying, rinsing, brushing, bathing, spreading, coating, impregnating and the like.

The precise instructions for pharmaceutical administration of the compounds and agents according to the invention necessarily depends on the requirements of the individual case, the nature of treatment, which can be, for example, preventive or curative, the species of organisms in question and of course the opinion of the treating doctor.

EXAMPLE 1

1-(2-(2,4-Dichlorophenyl-2-(3-phenylallylamino))ethyl-1H-imidazole (a)

1-(2-(2,4-Dichlorophenyl)-2-(3-phenylallylimino)ethyl-1H-imidazole 12.34 g (0.048 mol) of 2,4-dichlorophenacylimidazole and 6.66 g (0.05 mol) of cinnamylamine were suspended in 100 ml of toluene and the suspension was heated under reflux, using a water separator, until no further water of reaction was separated off. The solvent was removed in vacuo, after which 17.4 g (98% of theory) of a viscous oil were obtained.

(b)

1-(2-(2,4-Dichlorophenyl)-2-(3-phenylallylamino))ethyl-1H-imidazole 17.4 g (0.047 mol) of the product from stage (a) were dissolved in about 400 ml of methanol, the solution was cooled to 0° C. and 6.5 g (0.17 mol) of sodium borohydride were introduced in portions so that the temperature did not rise above 5° C. After removal of the cooling, the mixture was subsequently stirred at 20 to 30° C for 2 hours, the solvent was evaporated off and 150 ml of half-concentrated hydrochloric acid were added to the gelatinous residue in order to destroy excess sodium borohydride. A pH of 13 to 14 was then established with 40% strength aqueous sodium hydroxide solution, the aqueous basic solution was extracted several times with methylene chloride and the organic phase was washed with water, dried and evaporated.

The oily residue was taken up in acetone and concentrated nitric acid was added, whereupon the dinitrate of the compound precipitated as crystals.

Yield: 11.2 g (49% of theory).
Melting point: 190–192° C.

EXAMPLE 2

1-(2-(2,4-Dichlorophenyl)-2-(3-(4-chlorophenyl)allylamino))ethyl-1H-1,2,4-triazole (a)

1-(2-(2,4-Dichlorophenyl)-2-(3-(4-chlorophenyl)-2propenylideneimino))ethyl-1H-1,2,4-triazole 9.0 g (0.035 mol) of 1-(2-amino-2-(2,4-dichlorophenyl))ethyl-1H-1,2,4-triazole and 5.83 g (0.035 mol) of 4-chlorocinnamaldehyde were suspended in 80 ml of toluene and the suspension was heated under reflux, using a water separator, until no further water of reaction separated off. After removal of the solvent in vacuo, the oily residue was extracted by stirring in methanol, whereupon 14 g (98.5% of theory) of crystalline product of melting point 144 to 147° C. were obtained.

(b)

1-(2-(2,4-Dichlorophenyl)-2-(3-(4-chlorophenyl)allylamino))ethyl-1H-1,2,4-triazole 11.8 g (0.029 mol) of the product from stage (a) were suspended in 500 ml of methanol, the suspension was cooled to 0° C. and 3.78 g (0.1 mol) of sodium borohydride were introduced in portions so that the temperature did not rise above 5° C., a clear solution being formed. After removal of the cooling, the solution was subsequently stirred at 20 to 30° C. for about a further hour, the solvent was removed in vacuo and half-concentrated hydrochloric acid was added in order to destroy the excess sodium borohydride. A pH of 13 to 14 was then established by addition of 40% strength aqueous sodium hydroxide solution, the aqueous basic solution was extracted several times with methylene chloride and the organic phase was washed with water, dried and evaporated. The oily residue was taken up in acetone and concentrated nitric acid was added, whereupon the dinitrate of the compound precipitated as crystals.

Yield: 10.9 g (80% of theory).
Melting point: 195–197 C.

The compounds 3 to 27 listed in the table were prepared by one of the above procedures using the corresponding starting substances.

| No. | Ar | X | R | Ar' | Salt | Melting point (°C.) |
|---|---|---|---|---|---|---|
| 3 | 2,4-Dichlorophenyl | CH | Methyl | Phenyl | 2HNO$_3$ | 135–137 |
| 4 | 2,4-Dichlorophenyl | CH | H | 4-Tolyl | 2HNO$_3$ | 170–176 |
| 5 | 2,4-Dichlorophenyl | CH | H | 4-Methoxyphenyl | 2HNO$_3$ | 168–173 |
| 6 | 2,4-Dichlorophenyl | CH | H | 2-Chlorophenyl | 2HNO$_3$ | 170–195 |
| 7 | 2,4-Dichlorophenyl | CH | H | 4-Chlorophenyl | 2HNO$_3$ | 184–190 |
| 8 | 2,4-Dichlorophenyl | CH | Methyl | 4-Chlorophenyl | Base | Oil |
| 9 | 2,4-Dichlorophenyl | CH | H | 2,4-Dichlorophenyl | 2HNO$_3$ | 190–211 |
| 10 | 1-Naphthyl | CH | H | Phenyl | 2HNO$_3$ | 166–168 |
| 11 | 2-Thienyl | CH | H | Phenyl | Base | Oil |
| 12 | 2,4-Dichlorophenyl | CH | Propyl | Phenyl | Base | Oil |
| 13 | 2,4-Dichlorophenyl | N | H | Phenyl | 2HNO$_3$ | 139–149 |
| 14 | 2,4-Dichlorophenyl | N | Methyl | Phenyl | 2HNO$_3$.H$_2$O | 125–132 |
| 15 | 2,4-Dichlorophenyl | N | H | 4-Tolyl | 2HNO$_3$ | 165–173 |
| 16 | 2,4-Dichlorophenyl | N | H | 4-Methoxyphenyl | 2HNO$_3$ | 163–167 |
| 17 | 2,4-Dichlorophenyl | N | H | 2-Chlorophenyl | 2HNO$_3$ | 174–185 |
| 18 | 2,4-Dichlorophenyl | N | Methyl | 2-Chlorophenyl | 2HNO$_3$ | 119–124 |
| 19 | 2,4-Dichlorophenyl | N | H | 4-Chlorophenyl | Base | 77–110 |
| 20 | 2,4-Dichlorophenyl | N | Methyl | 4-Chlorophenyl | 2HNO$_3$ | 137–142 |
| 21 | 2,4-Dichlorophenyl | N | H | 2,4-Dichlorophenyl | HNO$_3$ | 184–220 |
| 22 | 2,4-Dichlorophenyl | N | Methyl | 2,4-Dichlorophenyl | Base | Oil |

-continued

| No. | Ar | X | R | Ar' | Salt | Melting point (°C.) |
|---|---|---|---|---|---|---|
| 23 | 2,4-Dichlorophenyl | N | H | 2,6-Dichlorophenyl | HNO₃ | 167–179 |
| 24 | 2,4-Dichlorophenyl | N | H | 3,4-Dichlorophenyl | HNO₃ | 181–204 |
| 25 | 2,4-Dichlorophenyl | N | H | 2-Nitrophenyl | HNO₃ | 193–205 |
| 26 | 2,4-Dichlorophenyl | N | H | 3-Nitrophenyl | 2HNO₃.H₂O | 173–178 |
| 27 | 2,4-Dichlorophenyl | N | H | 4-Bromo-2-thienyl | 2HNO₃ | 123–147 |

EXAMPLE 28

Emulsifiable concentrate
10% of the active compound No. 3
25% of 4-butyrolactone
55% of xylene
10% of Atlox 3335-B

EXAMPLE 29

Emulsifiable concentrate
25% of the active compound No. 2
20% of ethoxylated dinonylphenol (40 mol of ethylene oxide/mol of nonylphenol)
65% of dimethyl sulphoxide Emulsions of any desired concentration can be prepared with water from these concentrates.

EXAMPLE 30

Wettable powder
20% of the active compound No. 1
50% of kaolin
20% of Wessalon "SV"
10% of Arkopon I$^R$

EXAMPLE 31

Wettable powder
50% of the active compound No. 2
30% of kaolin
10% of Wessalon "SV"
10% of Arkopon I$^R$ The active compounds were intimately mixed with the additives in a mixer and the mixture was then ground via rolls and mills, which gave a wettable powder of outstanding wettability which can be diluted with water to give suspensions of any desired concentration.

The following test examples A to G relate to the new allylaminoethylazoles as fungicides in agriculture.

EXAMPLE A

In vitro tests (a) Cooled nutrient media were inoculated with an aqueous suspension of Hyphae portions and/or conidiospores of the particular test fungi. Filter platelets (diameter 5 mm) were impregnated in aqueous 0.001 to 0.2% dispersions of the active compound formulations and placed on the inoculated nutrient media. The minimum inhibitory concentration (MIC) was used for the evaluation. This is that concentration of active compound in the dispersion which completely prevents growth of the fungus.

The standards used were

| A Thiabendazole: | 2-(4-Thiazolyl)-benzimidazole |
|---|---|
| B Propiconazole: | 1-(2-(2,4-Dichlorophenyl)-4-propyl-1,3-dioxolan-2-ylmethyl)-1H-1,2,4-triazole |
| C Prochloraz: | 1-(N-Propyl-N-(2-(2,4,6-trichlorophenoxy)-ethyl-carbamoyl)-imidazole. |

The composition of the nutrient media used was as follows:

| Nutrient medium I: | peptone, biomalt, agar. |
|---|---|
| Nutrient medium II: | oatflake extract, agar. |
| Nutrient medium III: | carrot extract, potato extract, agar. |
| Nutrient medium IV: | biomalt, agar. |
| Nutrient medium V: | yeast extract, glucose, agar. |
| Nutrient medium VI: | peptone, biomalt, agar. |

Results

| | MIC (ppm a.s) | Nutrient medium |
|---|---|---|
| (1) *Alternaria alternata* | | |
| Standard C | 10 | II |
| Compound 1 | 10 | |
| (2) *Aspergillus niger* | | |
| Standard A | 100 | I |
| Compounds 1, 6 | 25 | |
| Compounds 5, 7 | 50 | |
| (3) *Botryotinia fuckeliana* | | |
| Standard A | 50 | I |
| Compound 1 | 10 | |
| Compounds 4, 7, 15 | 25 | |
| (4) *Cercospora beticola* | | |
| Standard C | 5–10 | III |
| Compounds 2, 3, 5, 6, 19, 20, 27 | 1 | |
| Compounds 1, 4, 15, 16, 17 | 2.5 | |
| Compounds 9, 14 | 5 | |
| Compound 4 | 10 | |
| (5) *Cochliobolus sativus* | | |
| Standard C | 10 | IV |
| Compound 19 | 5 | |
| Compounds 1, 2, 13 | 10 | |
| (6) *Fusarium culmorum* | | |
| Standard A | 100 | |
| Compounds 1, 3, 4, 5, 6 | 25 | |
| (7) *Fusarium oxysporum* | | |
| Standard A | 100 | II |
| Compounds 1, 14 | 50 | |
| (8) *Gibberella avenacea* | | |
| Standard A | 100 | II |
| Compound 1 | 10 | |
| (9) *Gibberella pulicaris* | | |
| Standard A | 100 | II |
| Compound 1 | 50 | |
| (10) *Monographella nivalis* | | |
| Standard A | 80 | II |
| Compounds 1, 6, 9 | 25 | |
| (11) *Phaeosphaeria nodorum* | | |
| Standard B | 50 | V |
| Compounds 1, 4, 5, 16, 19, 20 | 2.5 | |
| Compounds 2, 3, 7, 14, 16 | 5 | |
| Compounds 6, 13, 15 | 10 | |
| (12) *Pseudocercosporella herpotrichoides* | | |
| Standard A | 10 | II |
| Compound 13 | 10 | |
| (13) *Pyrenophora teres* | | |
| Standard A | 10 | V |
| Compounds 3, 4, 5, 6, 7 | 1 | |
| Compounds 1, 27 | 10 | |

-continued

| (14) *Venturia inaequalis* | | |
|---|---|---|
| Standard B | 10 | VI |
| Compounds 1, 15, 17, 24 | 2.5 | |

EXAMPLE B

Protective action of the compound against powdery mildew (*Erysiphe cichoracearum*) on cucumbers Cucumber plants 10 days old were sprayed with an aqueous dilution of formulated active compound.

After the spray coating had dried on, the plants were inoculated with conidiospores from infected cucumber plants. The treated plants then remained in a greenhouse under given conditions.

14 days after the artificial infection, the infestation with *Erysiphe cichoracearum* was evaluated.

In this test, for example, compounds 1 and 13 in an active compound concentration of 50 to 100 ppm were able to prevent an outbreak of the disease completely.

EXAMPLE C

Protective action of the compounds against cereal mildew (*Erysiphe graminis*) on wheat and barley Wheat and barley plants in the early 2-leaf stage were sprayed with an aqueous dilution of the formulated active compound until dripping wet. After the spray liquid had dried on, the plants were inoculated with conidiospores from infected plants. The treated plants then remained in a greenhouse under given conditions.

8 to 10 days after the artificial infection, the infestation with *Erysiphe graminis* was evaluated.

In this test, for example, the compounds 1, 13, 24 and 25 in an active compound concentration of 100 ppm were able to prevent an outbreak of the disease completely.

EXAMPLE D

Protective action of the compounds against brown rust (*Puccinia recondita*) on wheat Wheat plants in the early 2-leaf stage were sprayed with an aqueous dilution of the formulated active compound until dripping wet. After the spray liquid had dried on, inoculation was performed with uredospores obtained from infected plants. The test plants were then incubated in a climatically controlled chamber at 20° C. and about 95% atmospheric humidity for 24 hours.

The test plants stood under given conditions in the greenhouse until the disease had broken out completely on the control plants.

In this test, for example, the compounds 1, 2, 7, 10 and 13 in a concentration of 50 to 200 ppm completely prevented attack of the test plants.

EXAMPLE E

Protective action of the compounds against crown rust (*Puccinia coronata*) on oats Oat plants in the early 2-leaf stage were sprayed with an aqueous dilution of the formulated active compound until dripping wet. After the spray liquid had dried on, the inoculation was performed with uredospores obtained from infected plants. The test plants were then incubated in a climatically controlled chamber at 20° C. and about 95% atmospheric humidity for 24 hours.

The test plants stood under given conditions in a greenhouse until the disease had broken out completely on the control plants.

In this test, for example, the compounds 1, 10 and 13 in a concentration of 50 to 200 ppm sufficiently prevented infestation of the plants.

EXAMPLE F

Protective action of the compounds against leaf drought (*Phaeospohaeria nodorum*) on wheat Wheat plants in the early 2-leaf stage were sprayed with an aqueous dilution of the formulated active compound until dripping wet. After the spray liquid had dried on, the inoculation was performed with an aqueous suspension of pyknidiospores of *Phaeosphaeria nodorum*.

The test plants were then incubated in a climatically controlled chamber at 20° C. and about 95% atmospheric humidity for 36 to 48 hours.

The test plants stood under given conditions in a greenhouse until the disease had broken out completely on the control plants.

In this test, for example, the compounds 1, 6 and 13 in a concentration of 200 ppm of active substance completely or adequately prevented infestation of the plants.

EXAMPLE G

Protective action of the compounds against helminthosporiosis (*Cochliobolus sativus*) on wheat Wheat plants in the early 2-leaf stage were sprayed with an aqueous dilution of the formulated active compound until dripping wet. After the spray liquid had dried on, the inoculation was performed with an aqueous suspension of conidiospores of *Cochliobolus sativus*. The test plants were then incubated in a climatically controlled chamber at 20° C. and about 95% atmospheric humidity for 24 hours.

The test plants stood under given conditions in a greenhouse until the disease had broken out completely on the control plants.

In this test, for example, the compounds 1, 6 and 17 in a concentration of 200 ppm of active substance completely or adequately prevented infestation of the plants.

EXAMPLE H

Antimycotic action of the compounds against yeasts, moulds and dermatophytes

The substances were dissolved in dimethylsulphoxide and diluted with sterile water to various concentrations (0.19–100 μg/ml). In each case 0.5 ml of these dilutions were added to the liquid nutrient medium.

The individual strains were maintained on Sabouraud-beerwort slant agar and, before being used in the test, underwent a passage on a modified Sabouraud liquid nutrient medium, and were then harvested, washed and made up into a suspension of McFaerland 3 for the yeasts and moulds and a suspension of McFaerland 4 to 5 for the dermatophytes.

Each test tube was inoculated with 100 microliters of the prepared material (seed densities: yeasts about $10^3$/ml, moulds and dermatophytes about $10^3$/ml). The pH of the liquid nutrient medium was 6.0. After the inoculation, the fungi were incubated at 22° C. for 14 days.

The MIC value was used to determine the antimycotic activity of the compounds, and in particular that concentration stage at which macroscopically visible growth was no longer to be detected.

1-(2,4-Dichlorophenyl)-2-((2,4-dichlorophenyl)-methoxy-ethyl)-1H-imidazole nitrate) (compound A) was used as the comparison substance.

| MIC values | Results (micrograms/milliliter) | | | |
|---|---|---|---|---|
| Compound No. | 1 | 7 | 9 | A |
| *Trichophyton mentagrophytes* | 0.78 | 1.56 | 0.78 | 1.56 |
| *Trichophyton rubrum* | 0.78 | 0.78 | 0.39 | 6.25 |
| *Trichophyton verrucosum* | 0.78 | 1.56 | 0.78 | 6.25 |
| *Microsporum canis* | 0.78 | 6.25 | 3.12 | 6.25 |
| *Epidermophyton floccosum* | 0.78 | 0.78 | 0.39 | 1.56 |
| *Microsporum gypseum* | 0.78 | 3.12 | 3.12 | 3.12 |
| *Candida albicans* | 12.5 | 12.5 | 12.5 | 12.5 |
| *Candida tropicalis* | 6.25 | 6.25 | 6.25 | 12.5 |
| *Aspergillus fumigatus* | 0.78 | 12.5 | 25 | 3.12 |
| *Mucor mucedo* plus | 0.78 | 6.25 | 3.12 | 12.5 |
| *Mucor mucedo* minus | 0.78 | 6.25 | 3.12 | 12.5 |
| *Absidia ramosa* | 6.25 | 6.25 | 12.5 | 12.5 |

What we claim is:

1. An allylaminoethylimidazole of the formula:

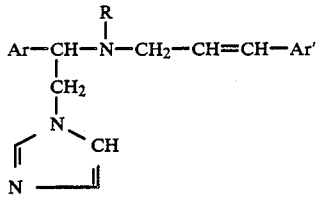

in which R is a hydrogen atom or an alkyl group containing 1 to 5 carbon atoms; each of Ar and Ar' is an unsubstituted phenyl group, a phenyl group substituted by one or more substituents selected from $C_1$-$C_3$ alkyl, $C_1$-$C_3$ alkoxy, nitro and halogen, an unsubstituted thienyl group, or a thienyl group substituted by halogen or naphthyl; or a phytophysiologically or pharmacologically tolerated acid addition salt thereof.

2. A compound of formula I according to claim 1, in which R is a hydrogen atom.

3. A compound of formula I according to claim 1, in which Ar is a 2,4-dichlorophenyl group.

4. 1-(2,4-Dichlorophenyl)-2-(3-phenylallylamino)-)ethyl-1H-imidazole.

5. A fungicidal agent comprising a fungicidally-effective amount of at least one compound of formula I according to claim 1 in admixture with inert auxiliaries and/or excipients.

6. An antimycotic agent comprising an antimycotic-effective amount of at least one compound of formula I according to claim 1 in admixture with inert auxiliaries and/or excipients.

7. A method of combating pathogenic fungi which comprises administering a fungicidally-effective amount of at least one compound of formula I according to claim 1 to said fungi or their environment.

8. A method for the treatment or prevention of a mycotic infection in a patient which comprises administering to the patient an antimycotic-effective amount of at least one compound of formula I according to claim 1.

* * * * *